(12) United States Patent
Gückel

(10) Patent No.: US 9,115,104 B2
(45) Date of Patent: *Aug. 25, 2015

(54) ETHYLENE OXIDE CATALYST WITH OPTIMIZED CESIUM CONTENT

(75) Inventor: Christian Gückel, München (DE)

(73) Assignee: Scientific Design Company, Inc., Little Ferry, NJ (US)

( * ) Notice: Subject to any disclaimer, the term of this patent is extended or adjusted under 35 U.S.C. 154(b) by 733 days.

This patent is subject to a terminal disclaimer.

(21) Appl. No.: 12/360,547

(22) Filed: Jan. 27, 2009

(65) Prior Publication Data

US 2010/0191006 A1    Jul. 29, 2010

(51) Int. Cl.
  *B01J 23/68* (2006.01)
  *C07D 301/10* (2006.01)
  *B01J 27/02* (2006.01)
  *B01J 27/12* (2006.01)
  *B01J 27/187* (2006.01)
  *B01J 35/10* (2006.01)
  *B01J 37/02* (2006.01)
  *B01J 37/08* (2006.01)

(52) U.S. Cl.
  CPC ............ *C07D 301/10* (2013.01); *B01J 23/688* (2013.01); *B01J 27/02* (2013.01); *B01J 27/12* (2013.01); *B01J 27/187* (2013.01); *B01J 35/109* (2013.01); *B01J 35/1095* (2013.01); *B01J 35/1009* (2013.01); *B01J 35/1014* (2013.01); *B01J 35/1038* (2013.01); *B01J 35/1042* (2013.01); *B01J 37/0201* (2013.01); *B01J 37/08* (2013.01)

(58) Field of Classification Search
  USPC ......... 502/208–211, 213, 216–223, 305, 308, 502/309, 311, 312, 317–323, 344–348, 353, 502/354
  See application file for complete search history.

(56) References Cited

U.S. PATENT DOCUMENTS

| | | | |
|---|---|---|---|
| 3,563,914 A | 2/1971 | Wattimena | |
| 3,702,259 A | 11/1972 | Nielsen | |
| 3,962,136 A | 6/1976 | Nielsen et al. | |
| 4,010,115 A | 3/1977 | Nielsen et al. | |
| 4,010,155 A | 3/1977 | Inouye et al. | |
| 4,012,425 A | 3/1977 | Nielsen et al. | |
| 4,039,561 A | 8/1977 | Mitsuhata et al. | |
| 4,066,575 A | 1/1978 | Winnick | |
| 4,123,385 A | 10/1978 | Rebsdat et al. | |
| 4,350,616 A | 9/1982 | Boussert | |
| 4,761,394 A | 8/1988 | Lauritzen | |
| 4,766,105 A | 8/1988 | Lauritzen | |
| 4,808,738 A | 2/1989 | Lauritzen | |
| 4,820,675 A | 4/1989 | Lauritzen | |
| 4,829,043 A * | 5/1989 | Boehning et al. | 502/348 |
| 4,833,261 A | 5/1989 | Lauritzen | |
| 4,908,343 A | 3/1990 | Bhasin | |
| 5,011,807 A | 4/1991 | Hayden et al. | |
| 5,057,481 A | 10/1991 | Bhasin | |
| 5,099,041 A | 3/1992 | Hayden et al. | |
| 5,102,848 A | 4/1992 | Soo et al. | |
| 5,187,140 A | 2/1993 | Thorsteinson et al. | |
| 5,407,888 A | 4/1995 | Herzog et al. | |
| 7,247,600 B2 * | 7/2007 | Lockemeyer | 502/347 |
| 7,696,368 B2 * | 4/2010 | Billig et al. | 549/534 |
| 7,803,957 B2 * | 9/2010 | Rizkalla et al. | 549/536 |
| 7,932,408 B2 * | 4/2011 | Guckel | 549/536 |
| 7,977,274 B2 * | 7/2011 | Gueckel | 502/243 |
| 2003/0162984 A1 | 8/2003 | Lockemeyer et al. | |
| 2007/0184973 A1 | 8/2007 | Lockemeyer et al. | |
| 2008/0081920 A1 | 4/2008 | Gueckel | |
| 2008/0306291 A1 * | 12/2008 | Billig et al. | 549/536 |

FOREIGN PATENT DOCUMENTS

| | | |
|---|---|---|
| CN | 101085425 | 12/2007 |
| CN | 100408168 C | 8/2008 |
| WO | WO03072246 A2 | 9/2003 |
| WO | WO2009029414 A1 | 3/2009 |
| WO | WO2009029419 A1 | 3/2009 |

OTHER PUBLICATIONS

International Search Report dated Aug. 13, 2010.
Supplementary European Search Report dated Jun. 14, 2012 received in a corresponding foreign application.
Chinese Office Action dated Dec. 18, 2012 and a translation of portions of the Office Action received in a corresponding foreign application.
European Office Action dated Dec. 16, 2014 received in related application EP 10 736 166.9-1501.

* cited by examiner

*Primary Examiner* — Anthony J Zimmer
(74) *Attorney, Agent, or Firm* — Scully, Scott, Murphy & Presser, P.C.

(57) ABSTRACT

The invention is directed to a catalyst useful in the epoxidation of an olefin to an olefin oxide, the catalyst comprising a support having a multimodal pore size distribution comprising a first and a second distribution of pore sizes wherein each distribution of pore sizes possesses a different mean pore size and a different pore size of maximum concentration, the support having a catalytically effective amount of silver, a promoting amount of rhenium, and cesium in an amount up to, but not exceeding 700 ppm disposed thereon. The invention is also directed to methods for using the catalyst for the commercial production of an olefin oxide from olefin and oxygen-containing feed gases.

34 Claims, No Drawings

ETHYLENE OXIDE CATALYST WITH OPTIMIZED CESIUM CONTENT

FIELD OF THE INVENTION

The present invention generally relates to silver-based ethylene oxide catalysts, and more specifically, to the high selectivity versions of these catalysts additionally containing rhenium and cesium as promoters.

BACKGROUND OF THE INVENTION

The catalytic epoxidation of an olefin by use of silver-based catalysts is well known in the art. However, conventional silver-based catalysts are often limited by their low selectivities. To a large extent, the selectivity determines the economical feasibility of an epoxidation process. For example, a one percent improvement in the selectivity of the epoxidation process can substantially reduce the yearly operating costs of a large-scale olefin oxide plant.

As is known to those skilled in the art, the produced epoxide is highly valuable. For example, the ethylene oxide may be reacted with water, an alcohol, or an amine to form ethylene glycol, a 1,2-diol ether, or an alkanolamine, respectively. Ethylene glycol, in turn, is used, for example, as a component in antifreeze compositions, or as a solvent, or a base material in the production of polyethylene terephthalates.

Highly selective silver-based epoxidation catalysts have been developed which extend the selectivity to a value that is closer to the stoichiometric limit. Such highly selective catalysts comprise a porous refractory support, such as alpha alumina, along with a catalytic amount of silver on its surface and at least one promoter that improves the catalyst performance in the epoxidation process.

The use of alkali and transition metals as promoters for silver catalysts is now common in the production of ethylene oxide by the partial oxidation of ethylene in the vapor phase. See, for example, U.S. Pat. Nos. 4,010,155, 4,012,425, 4,123,385, 4,066,575, 4,039,561 and 4,350,616. Highly selective catalysts which contain, in addition to silver, selectivity-enhancing promoters, such as rhenium, molybdenum, tungsten or nitrate- or nitrite-forming compounds, are discussed in U.S. Pat. Nos. 4,761,394 and 4,766,105. The catalyst may comprise further elements as described in U.S. Pat. Nos. 3,962,136 and 4,010,115.

Over the last two decades, rhenium has been shown to be effective in improving the selectivity of silver-based catalysts supported by a refractory porous support. See, for example, U.S. Pat. Nos. 4,761,394 and 4,833,261. Further improvement of silver-based catalysts promoted with rhenium has been achieved by the use of sulfur (S), molybdenum (Mo), tungsten (W), chromium (Cr) promoters, as disclosed in, for example, U.S. Pat. Nos. 4,766,105, 4,820,675 and 4,808,738.

In view of the above, there is a continuing need for silver-based epoxidation catalysts with improved performance, particularly in catalyst activity and selectivity.

SUMMARY OF THE INVENTION

It has now been found that, by controlling the pore size distribution and cesium content in silver-based catalysts containing at least rhenium and cesium, a catalyst can be provided with an optimal level of activity, and hence, selectivity. Both the pore size distribution and the cesium content significantly impact the catalyst activity. For example, a bimodal pore size distribution in the carrier has been found to be highly beneficial in optimizing the activity and selectivity of the catalyst. However, if the cesium concentration is too high, the activity is adversely reduced and the catalyst requires operation at higher temperatures to maintain the productivity at the design level. In some instances, when the cesium content is too high, the catalyst is not able to reach the design level within normal operating conditions. Because of the high operating temperatures associated with these catalysts, the selectivity is also affected negatively.

The invention advantageously provides a silver-based catalyst having a bimodal pore size distribution and a cesium content that have been optimized to provide a catalyst with an optimal level of activity. The optimal level of activity provides a catalyst with high selectivity and high productivity, and which is capable of operating under the typical operating conditions known in the art.

In a preferred embodiment, the present invention is directed to a catalyst useful in the epoxidation of an olefin to an olefin oxide, the catalyst comprising a support having a multimodal pore size distribution comprising a first and a second distribution of pore sizes wherein each distribution of pore sizes possesses a different mean pore size and a different pore size of maximum concentration, the support having a catalytically effective amount of silver, a promoting amount of rhenium, and cesium in an amount up to, but not exceeding 700 ppm disposed thereon. In particular preferred embodiment, the catalyst contains a support having a bimodal pore size distribution, with a first mode of pores having a mean pore diameter ranging from about 0.01 μm to about 5 μm and a second mode of pores having a mean pore diameter ranging from about 5 μm to about 30 μm. The catalyst includes a catalytically effective amount of silver, a promoting amount of rhenium, and cesium in an amount up to, but not exceeding 700 ppm disposed thereon. The present invention is also directed to methods for using the catalyst for the commercial production of an olefin oxide from olefin and oxygen-containing feed gases.

DETAILED DESCRIPTION OF THE INVENTION

In one aspect, the invention is directed to a catalyst (i.e., silver-based epoxidation catalyst) useful in the conversion of an olefin to an olefin oxide. The catalyst contains at least the following four components: i) a refractory support, ii) a catalytically-effective amount of silver thereon, iii) a promoting amount of rhenium thereon, and iv) an effective amount of cesium, all of which are further described below.

The support employed in this invention may be selected from a large number of solid, refractory supports that are porous. The support may comprise materials such as, for example, alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics, and combination thereof. The preferred support is comprised of alpha-alumina having a very high purity; i.e., at least 95 wt. % pure, or more preferably, at least 98 wt. % purity. The remaining components may include inorganic oxides other than alpha-alumina, such as silica, alkali metal oxides (e.g., sodium oxide) and trace amounts of other metal-containing or non-metal-containing additives or impurities. The alumina support may also contain various impurities and additives that may or may not influence the catalytic epoxidation reaction.

In the process of preparing the preferred alumina support, high-purity aluminum oxide, preferably alpha-alumina, is usually mixed with temporary and permanent binders. The temporary binders, also known as burnout materials, are thermally decomposable organic compounds of moderate to high molecular weight which, on decomposition, alter the pore structure of the support. They are essentially completely removed during firing when producing the final support. Some examples of burnout materials include cellulose, substituted celluloses, e.g., methylcellulose, ethylcellulose, and carboxyethylcellulose, stearates (e.g., organic stearate esters, such as methyl or ethyl stearate), waxes, granulated polyolefins (e.g., polyethylene and polypropylene), walnut shell flour, and the like, which are decomposable at the firing temperatures used in preparation of the support.

The permanent binders are typically inorganic clay-type materials having fusion temperatures below that of the alumina, such as silica with one or more alkali metal compounds. They typically impart mechanical strength to the finished support. Preferably, the binding materials are used in sufficient amounts so as to substantially prevent the formation of crystalline silica compounds. A particularly convenient binder material is a mixture of boehmite, an ammonia stabilized silica sol, and a soluble sodium salt.

After thorough dry-mixing, sufficient water and/or other suitable liquid is added to help form the mass into a paste-like substance. Catalyst support particles are formed from the paste by conventional means, such as extrusion. After molding into the desired shape, the support particles are calcined at a temperature from about 1200° C. to about 1600° C. to form the support. When the particles are formed by extrusion, it may be desirable to also include extrusion aids. The amounts of extrusion aids required depend on a number of factors that relate to the equipment used. Such factors are well within the general knowledge of a person skilled in the art of extruding ceramic materials. After firing, the support is preferably washed to remove soluble residues. Washing is most commonly done with water, but washing with other solvents or aqueous/non-aqueous solutions can also be beneficial.

The solid support (carrier) employed in the present invention has a multimodal pore size distribution (i.e., different pore size ranges, each range possessing a different pore size of maximum concentration). The multimodal pore size distribution is at least bimodal, and can thus be trimodal, tetramodal, or of a higher modality. The multimodal pore size distribution is characterized by the presence of at least two distributions (modes) of pore sizes, each pore size distribution being either overlapping or non-overlapping with another pore size distribution, and each pore size distribution having its own range of pore sizes (pore diameters) and peak concentration (typically expressed as peak pore volume). Each pore size distribution can be characterized by a single mean pore size (mean pore diameter) value. Accordingly, a mean pore size value given for a pore size distribution necessarily corresponds to a range of pore sizes that result in the indicated mean pore size value.

The carrier can have any suitable distribution of pore diameters. As used herein, the "pore diameter" is used interchangeably with "pore size". Typically, the pore diameters for each range are at least about 0.01 microns (0.01 µm), and more typically, at least about 0.1 µm. In different embodiments, the pore diameters can be at least about 0.2 µm, or 0.3 µm, or 0.4 µm, or 0.5 µm, or 0.6 µm, or 0.7 µm, or 0.8 µm, or 0.9 µm, or 1.0 µm, or 1.5 µm, or 2.0 µm. Typically, the pore diameters are no more than about 50 µm, 40 µm, 30 µm, 20 µm, or 10 µm. In particular embodiments, the pore diameters are no more than about 9 µm, or 8 µm, or 7 µm, or 6 µm, or 5 µm, or 4 µm, or 3 µm, or 2.5 µm. Any range derived from the foregoing minimum and maximum exemplary values is also suitable herein. In different embodiments, the suitable pore diameter range for each mode of pores can be independently selected from, for example, 0.01-50 µm, 1-50 µm, 2-50 pm, 5-50 µm, 10-50 µm, 20-50 µm, 30-50 µm, 0.01-40 µm, 1-40 µm, 2-40 µm, 5-40 µm, 10-40 µm, 20-40 µm, 30-40 µm, 0.01-30 µm, 0.05-30 µm, 0.1-30 µm, 0.5-30 µm, 0.1-30 µm, 1-30 µm, 2-30 µm, 3-30 µm, 4-30 µm, 5-30 µm, 10-30 µm, 15-30 µm, 20-30 µm, 0.01-10 µm, 0.05-10 µm, 0.1-10 µm, 0.5-10 µm, 1-10 µm, 2-10 µm, 3-10 µm, 4-10 µm, 5-10 µm, 6-10 µm, 7-10 µm, 8-10 µm, 9-10 µm, 0.01-8 µm, 0.05-8 µm, 0.1-8 µm, 0.5-8 µm, 1-8 µm, 1.5-8 µm, 2-8 µm, 2.5-8 µm, 3-8 µm, 4-8 µm, 5-8 µm, 6-8 µm, 7-8 µm, 0.01-6 µm, 0.05-6 µm, 0.1-6 µm, 0.5-6 µm, 1-6 µm, 1.5-6 µm, 2-6 µm, 2.5-6 µm, 3-6 µm, 4-6 µm, 5-6 µm, 0.01-5 µm, 0.05-5 µm, 0.1-5 µm, 0.5-5 µm, 1-5 µm, 1.5-5 µm, 2-5 µm, 2.5-5 µm, 3-5 µm, 3.5-5 µm, 4-5 µm, 0.01-4 µm, 0.05-4 µm, 0.1-4 µm, 0.5-4 µm, 1-4 µm, 1.5-4 µm, 2-4 µm, 2.5-4 µm, 3-4 µm, 3.5-4 µm, 0.01-3 µm, 0.05-3 µm, 0.1-3 µm, 0.5-3 µm, 1-3 µm, 1.5-3 µm, 2-3 µm, 2.5-3 µm, 0.01-2 µm, 0.05-2 µm, 0.1-2 µm, 0.5-2 µm, 1-2 µm, and 1.5-2 µm, as long as the range of each mode of pores is different and each range possesses a different pore size of maximum concentration.

The first mode and second mode of pores possess different mean pore sizes (i.e., different mean pore diameters). Preferably, at least one of the modes of pores has a mean pore diameter within the range of about 0.01 µm to about 5 µm. More preferably, both a first and second mode of pores have a mean pore diameter within the range of about 0.01 µm to about 5 µm as long as the mean pore diameters are different. For example, at least one of the first and second mode of pores can have a mean pore size of about 0.01 µm, 0.02 µm, 0.03 µm, 0.04 µm, 0.05 µm, 0.06 µm, 0.07 µm, 0.08 µm, 0.09 µm, 0.1 µm, 0.2 µm, 0.3 µm, 0.4 µm, 0.5 µm, 0.6 µm, 0.7 µm, 0.8 µm, 0.9 µm, 1.0 µm, 1.1 µm, 1.2 µm, 1.3 µm, 1.4 µm, 1.5 µm, 1.6 µm, 1.7 µm, 1.8 µm, 1.9 µm, 2.0 µm, 2.1 µm, 2.2 µm, 2.3 µm, 2.4 µm, 2.5 µm, 2.6 µm, 2.7 µm, 2.8 µm, 2.9 µm, 3.0 µm, 3.1 µm, 3.2 µm, 3.3 µm, 3.4 µm, 3.5 µm, 3.6 µm, 3.7 µm, 3.8 µm, 3.9 µm, 4.0 µm, 4.1 µm, 4.2 µm, 4.3 µm, 4.4 µm, 4.5 µm, 4.6 µm, 4.7 µm, 4.8 µm, 4.9 µm, or 5.0 µm. Two or more modes of pores can also be independently selected from any of the above mean pore sizes as long as the mean pore sizes for each mode of pores are different. Any range derived from any two values recited above are also contemplated herein.

In another embodiment, at least one mode of pores is characterized by having a mean pore diameter above 5 µm up to about 30 µm. For example, in different embodiments, at least one mode of pores can have a mean pore diameter above 5 µm to about 25 µm, or above 5 µm to about 20 µm, or above 5 µm to about 15 µm, or above 5 µm to about 10 µm, or about 6 µm to about 30 µm, or about 7 µm to about 30 µm, or about 8 µm to about 30 µm, or about 10 µm to about 30 µm, or about 10 µm to about 25 µm, or about 10 µm to about 20 µm, or about 15 µm to about 30 µm. In one embodiment, one mode of pores has a mean pore diameter within the range of about 0.01 µm to about 5 µm (or any of the specific exemplary values given above within this range, or sub-ranges derived therefrom) while another mode of pores has a mean pore diameter above 5 µm up to about 30 µm, or any of the sub-ranges given therein. In another embodiment, at least two modes of pores have a mean pore diameter above 5 µm up to about 30 µm.

In a first embodiment, the first mode of pores comprises at most about 50% of the total pore volume and the second mode of pores comprises at least about 50% of the total pore volume. In a second embodiment, the first or second mode of pores comprises at most about 45% of the total pore volume and the other mode of pores comprises at least about 55% of the total pore volume. In a third embodiment, the first or second mode of pores comprises at most about 40% of the total pore volume and the other mode of pores comprises at least about 60% of the total pore volume. In a fourth embodiment, the first or second mode of pores comprises at most about 35% of the total pore volume and the other mode of pores comprises at least about 65% of the total pore volume. In a fifth embodiment, the first or second mode of pores comprises at most about 30% of the total pore volume and the other mode of pores comprises at least about 70% of the total pore volume. Numerous other embodiments reflective of different bimodal pore distributions are possible and within the scope of the present invention. Without wishing to be bound by any theory, it is believed that a catalyst with the described bimodal pore size distribution possesses a type of pore structure in which reaction chambers are separated by diffusion channels. The pore volume and pore size distribution described herein can be measured by any suitable method, but are more preferably obtained by the conventional mercury porosimeter method as described in, for example, Drake and Ritter, *Ind. Eng. Chem. Anal. Ed.*, 17, 787 (1945).

Preferably, the mean pore diameter of the first mode of pores and the mean pore diameter of the second mode of pores (i.e., the "differential in mean pore diameters") are different by at least about 0.1 µm. In different embodiments, the difference in mean pore sizes can be at least, for example, 0.2 µm, or 0.3 µm, or 0.4 µm, or 0.5 µm, or 0.6 µm, or 0.7 µm, or 0.8 µm, or 0.9 µm, or 1.0 µm, or 1.2 µm, or 1.4 µm, or 1.5 µm, 1.6 µm, or 1.8 µm, or 2.0 µm, or 2.5 µm, or 3 µm, or 4 µm, or 5 µm, or 6 µm, or 7 µm, or 8 µm, or 9 µm, or 10 µm, and up to about 15, 20 or 30 µm.

The final support typically possesses a water absorption value ranging from about 0.2 cc/g to about 0.8 cc/g, and more typically from about 0.25 cc/g to about 0.6 cc/g. The support preferably has a B.E.T. surface area of at most 20 $m^2/g$, more preferably at most 10 $m^2/g$, more preferably at most 5 $m^2/g$, and more preferably at most 1 $m^2/g$. In different embodiments, the B.E.T. surface area can be preferred to be in the range of, for example, 0.1 to 2.0 $m^2/g$, or 0.1 to 1.5 $m^2/g$, or 0.1 to 1.0 m/g, or 0.2 to 1.0 $m^2/g$, or 0.5 to 1 $m^2/g$. Suitable porosity volumes measured by mercury intrusion techniques are generally in the range of about 0.2 ml/g to about 0.8 ml/g, and preferably from about 0.25 ml/g to about 0.60 ml/g. The B.E.T. surface area described herein can be measured by any suitable method, but is more preferably obtained by the method described in Brunauer, S., et al., *J. Am. Chem. Soc.*, 60, 309-16 (1938).

The carrier of the invention can be of any suitable shape or morphology. For example, the carrier can be in the form of particles, chunks, pellets, rings, spheres, three-holes, wagon wheels, cross-partitioned hollow cylinders, and the like, of a size preferably suitable for employment in fixed bed reactors. Typically, carrier particles have equivalent diameters in the range of from about 3 mm to about 12 mm, and more typically in the range of from about 5 mm to about 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object.

Suitable supports having the properties described above can be prepared as described, or obtained by, for example, Saint-Gobain Norpro Co., Sud Chemie AG, Noritake Co., CeramTec AG, and Industrie Bitossi S.p.A.

In order to produce the catalyst, a carrier having the above characteristics is then provided with a catalytically effective amount of silver. The silver can be located on the surface and/or throughout the pores of the refractory support. A catalytically effective amount of silver can be, for example, up to about 45% by weight of silver, expressed as metal, based on the total weight of the catalyst including the support. Silver contents, expressed as metal, of from about 1% to about 40% based on the total weight of the catalyst, are more typical. In other embodiments, the silver content can be from, for example, about 1 to 35%, 5 to 35%, 1 to 30%, 5 to 30%, 1 to 25%, 5 to 25%, 1 to 20%, 5 to 20%, 8 to 40%, 8 to 35%, 8 to 30%, 10 to 40%, 10 to 35%, 10 to 25%, 10 to 20%, 12 to 40%, 12 to 35%, 12 to 30%, or 12 to 25%.

The carrier can be impregnated and incorporated with silver, along with any desired promoters, by any of the conventional methods known in the art, e.g., by excess solution impregnation, incipient wetness impregnation, spray coating, and the like. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Preferably, the catalyst is prepared by impregnating the support with a silver compound, complex, or salt dissolved in a suitable solvent sufficient to cause deposition of a silver-precursor compound onto the support. Preferably, an aqueous silver solution is used. Typically, the carrier material is placed in contact with the silver-containing solution until a sufficient amount of the solution is absorbed by the carrier. Preferably, the quantity of the silver-containing solution used to impregnate the carrier is no more than is necessary to fill the pore volume of the carrier. Infusion of the silver-containing solution into the carrier can be aided by application of a vacuum. After impregnation, the excess solution is removed from the impregnated support, and the impregnated support is heated to evaporate the solvent and to deposit the silver or silver compound on the support as is known in the art.

Silver compounds useful for impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. Some examples of water-based solvents include water and water-alcohol mixtures. Some examples of organic-based solvents include, but are not limited to, alcohols (e.g., alkanols), glycols (e.g., alkyl glycols), ketones, aldehydes, amines, tetrahydrofuran, nitrobenzene, nitrotoluene, glymes (e.g., glyme, diglyme and tetraglyne), and the like, and their combinations. Organic-based solvents that have 1 to about 8 carbon atoms per molecule are preferred.

A wide variety of complexing or solubilizing agents may be employed to solubilize silver to the desired concentration in the impregnating medium. Useful complexing or solubilizing agents include organic amines, ammonia, lactic acid and combinations thereof. For example, the complexing agent can be an alkylene diamine having from 1 to 5 carbon atoms. In a preferred embodiment, the solution comprises an aqueous solution of silver oxalate and ethylene diamine. The complexing/solubilizing agent may be present in the impregnating solution in an amount from about 0.1 to about 5.0 moles of ethylene diamine per mole of silver, preferably from about 0.2 to about 4.0 moles, and more preferably from about 0.3 to about 3.0 moles of ethylene diamine for each mole of silver. The concentration of silver salt in the solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

Also deposited on the support, either prior to, coincidentally with, or subsequent to the deposition of the silver is a promoting amount of a rhenium (Re) component, which may be a rhenium-containing compound, complex, or material. The Re promoter may be present in an amount from about 0.001 wt. % to about 1 wt. %, preferably from about 0.005 wt. % to about 0.5 wt. %, and more preferably from about 0.01 wt. % to about 0.1 wt. %, expressed as the Re metal, based on the total weight of the catalyst including the support.

Also deposited on the support either prior to, coincidentally with, or subsequent to the deposition of the silver and rhenium is a promoting amount of cesium (Cs) in a concentration up to, but not exceeding 700 ppm. Preferably, the Cs concentration is not less than about 350 ppm. Within this range, the catalyst performance is acceptable or optimum with respect to both selectivity and activity. A cesium concentration outside of this range can be used but is not preferred since it can be expected that either the selectivity or the activity will decline below an acceptable or optimum level. Without limiting the scope of the invention, it is believed that the activity is positively influenced by a lower cesium concentration while the selectivity is negatively influenced by a lower cesium concentration. It was found that within the Cs concentration range of 350-700 ppm both parameters are within acceptable levels.

In different embodiments, Cs can be in a promoting amount up to, but not exceeding, for example, about 650 ppm, or 600 ppm, or 550 ppm, or 500 ppm, or 450 ppm, or 400 ppm.

Other promoting species can optionally also be deposited on the support either prior to, coincidentally with, or subsequent to the deposition of the silver, rhenium, and cesium. The support may be impregnated at the same time or in separate steps with the various catalyst promoters. As used herein, a "promoting amount" of a certain component of a catalyst refers to an amount of that component that works effectively to provide an improvement in one or more of the catalytic properties of the catalyst when compared to a catalyst not containing said component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, promoting amounts of an alkali metal or mixtures of two or more alkali metals, other than Cs can also be included. Some examples of other alkali metal promoters include, for example, lithium, sodium, potassium, rubidium, and combinations thereof. The amount of alkali metal preferably ranges from about 10 ppm to about 3000 ppm, more preferably about 10 ppm to about 2000 ppm, more preferably from about 10 ppm to about 1500 ppm, more preferably from about 10 ppm to about 1000 ppm, and even more preferably from about 10 ppm to about 400 ppm by weight of the total catalyst, expressed in terms of the alkali metal.

The catalyst may also include a promoting amount of a Group IIA alkaline earth metal or a mixture of two or more Group IIA alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The catalyst may also include a promoting amount of a main group element or a mixture of two or more main group elements. Suitable main group elements include any of the elements in Groups IIIA (boron group) to VIIA (halogen group) of the Periodic Table of the Elements. For example, the catalyst can include a promoting amount of one or more sulfur compounds, one or more phosphorus compounds, one or more boron compounds, one or more halogen-containing compounds, or combinations thereof. The catalyst can also include a main group element, aside from the halogens, in its elemental form.

The catalyst may also include a promoting amount of a transition metal or a mixture of two or more transition metals other than Re. Suitable transition metals can include, for example, the elements from Groups IIIB (scandium group), IVB (titanium group), VB (vanadium group), VIB (chromium group), VIIB (manganese group), VIIIB (iron, cobalt, nickel groups), IB (copper group), and IIB (zinc group) of the Periodic Table of the Elements, as well as combinations thereof. More typically, the additional transition metal is an early transition metal, i.e., from Groups IIIB, IVB, VB or VIB, such as, for example, hafnium, yttrium, molybdenum, tungsten, chromium, titanium, zirconium, vanadium, tantalum, niobium, or a combination thereof.

The catalyst may also include a promoting amount of a rare earth metal or a mixture of two or more rare earth metals. The rare earth metals include any of the elements having an atomic number of 57-103. Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

After impregnation with silver and any promoters, the impregnated carrier is removed from the solution and calcined for a time sufficient to reduce the silver component to metallic silver and to remove volatile decomposition products from the silver-containing support. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a pressure in a range from about 0.5 to about 35 bar. In general, the higher the temperature, the shorter the required calcination period. A wide range of heating periods have been described in the art for the thermal treatment of impregnated supports. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose.

During calcination, the impregnated support may be exposed to a gas atmosphere comprising an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcination. Non-limiting examples include nitrogen, argon, krypton, helium, and combinations thereof; with the preferred inert gas being nitrogen. Non-limiting examples of the oxygen-containing oxidizing component include molecular oxygen ($O_2$), $CO_2$, NO, $NO_2$, $N_2O$, $N_2O_3$, $N_2O_4$, or $N_2O_5$, or a substance capable of forming NO, $NO_2$, $N_2O$, $N_2O_3$, $N_2O_4$, or $N_2O_5$ under the calcination conditions, or combinations thereof, and optionally comprising $SO_3$, $SO_2$ or combinations thereof. In some embodiments, a combination of $O_2$ with NO or $NO_2$ is used. In one embodiment, the atmosphere comprises from about 10 ppm to about 1% by volume of an oxygen-containing oxidizing component. In another embodiment, the atmosphere comprises from about 50 ppm to about 500 ppm of an oxygen-containing oxidizing component.

In another embodiment, the impregnated support, which has been calcined as disclosed above, may optionally thereafter be contacted with an atmosphere comprising a combination of oxygen and steam, the atmosphere being substantially absent of an olefin, and preferably, completely absent of an olefin. The atmosphere usually comprises from about 2% to about 15% steam by volume, preferably from about 2% to about 10% steam by volume, and more preferably from about 2% to about 8% steam by volume. The atmosphere typically comprises from about 0.5% to about 30% oxygen by volume, preferably from about 1% to about 21% oxygen by volume, and more preferably from about 5% to about 21% oxygen by volume. The balance of the gas atmosphere may be comprised of an inert gas. Non-limiting examples of the inert gas include nitrogen, argon, krypton, helium, and combinations thereof with the preferred inert gas being nitrogen. The contacting is usually conducted at a temperature from about 200° C. or higher. In one embodiment, the contacting is conducted at a temperature from about 200° C. to about 350° C. In another embodiment, the contacting is conducted at a temperature from about 230° C. to about 300° C. In another embodiment, the contacting is conducted at a temperature from about 250° C. to about 280° C. In yet another embodiment, the contacting is conducted at a temperature from about 260° C. to about 280° C. Typically, the contacting is conducted for about 0.15 hours or more. In one embodiment, the contacting is conducted for about 0.5 to about 200 hours. In another embodiment, the contacting is conducted for about 3 to about 24 hours. In another embodiment, the contacting is conducted for about 5 to about 15 hours.

In another aspect, the invention is directed to methods for epoxidizing an olefin by contacting the olefin (e.g., ethylene) and oxygen-containing feed gases with the inventive catalyst described above under suitable conditions. In one embodiment, the epoxidation process is conducted by continuously contacting the oxygen-containing gas and olefin with the catalyst. Oxygen may be supplied to the reaction in substantially pure molecular form or in a mixture such as air. Molecular oxygen employed as a reactant may be obtained from conventional sources. By way of example, reactant feed mixtures may contain from about 0.5% to about 45% ethylene and from about 3% to about 15% oxygen, with the balance comprising comparatively inert materials including such substances as carbon dioxide, water, inert gases, other hydrocarbons, and one or more reaction modifiers (e.g., reaction moderators), such as organic halides. Non-limiting examples of inert gases include nitrogen, argon, helium and mixtures thereof. Non-limiting examples of the other hydrocarbons include methane, ethane, propane, and mixtures thereof. Carbon dioxide and water are byproducts of the epoxidation process as well as common contaminants in the feed gases. Both have adverse effects on the catalyst, so the concentrations of these components are usually kept at a minimum. Non-limiting examples of reaction moderators include organic halides such as $C_1$ to $C_8$ halohydrocarbons. Preferably, the reaction moderator is methyl chloride, ethyl chloride, ethylene dichloride, ethylene dibromide, vinyl chloride, or mixtures thereof. Some preferred reaction moderators include ethyl chloride and ethylene dichloride. The reaction moderators are typically employed in amounts of about 0.3 to about 20 ppmv, and more typically, from about 0.5 to about 15 ppmv of the total volume of the feed gas.

A typical method for the ethylene epoxidation process comprises the vapor-phase oxidation of ethylene with molecular oxygen, in the presence of the inventive catalyst, in a fixed-bed tubular reactor Conventional, commercial fixed-bed ethylene-oxide reactors are typically in the form of a plurality of parallel elongated tubes (in a suitable shell) approximately 0.7 to 2.7 inches O.D. and 0.5 to 2.5 inches I.D. and 15-53 feet long filled with catalyst. Such reactors include a reactor outlet which allows the olefin oxide, unused reactant, and byproducts to exit the reactor chamber.

Typical operating conditions for the ethylene epoxidation process involve temperatures in the range of about 180° C. to about 330° C., and preferably, about 200° C. to about 325° C., and more preferably about 220° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 0.1 to about 5 seconds. The present catalysts are effective for this process when operated within these ranges of conditions.

The resulting ethylene oxide, which exits the reactor through the reactor outlet, is separated and recovered from the reaction products using conventional methods. For this invention, the ethylene epoxidation process may include a gas recycle process wherein a portion or substantially all of the reactor effluent is readmitted to a reactor inlet after substantially or partially removing the ethylene oxide product and the byproducts including carbon dioxide. In the recycle mode, carbon dioxide concentrations in the gas inlet to the reactor may be, for example, from about 0.3 to about 5 volume percent.

The inventive catalysts have been shown to be particularly selective for oxidation of ethylene with molecular oxygen to ethylene oxide especially at high ethylene and oxygen conversion rates. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production rate (work rate) of 7-20 lbs. EO/cu.ft. catalyst/hr. The feed composition at the reactor inlet may typically comprises 1-45% ethylene, 3-15% $O_2$, 0.3-40% $CO_2$, 0-3% ethane, 0.3-20 ppmv total concentration of organic chloride moderator(s), and the balance of the feed being comprised of argon, methane, nitrogen or mixtures thereof.

Examples have been set forth below for the purpose of further illustrating the invention. The scope of this invention is not to be in any way limited by the examples set forth herein.

Example 1

Catalyst Performance for Different Cesium Levels

Silver Solution

An 834 g portion of high purity silver oxide (Ames Goldsmith Corp.) was added to a stirred solution of 442 g oxalic acid dehydrate (ACS Certified Reagent, Fisher) in about 2,800 g deionized water. A precipitate of hydrated silver oxalate salt formed on mixing. Stirring was continued for 0.5 hours. The precipitate was then collected on a filter and washed with deionized water. Analysis showed that the precipitate contained 50.5 wt % silver. Next, 213.9 g of the silver oxalate precipitate was dissolved in a mixture of 77.2 grams ethylenediamine (99+%, Aldrich) and 60.3 g deionized water. The temperature of the solution was kept below 40° C. by combining the reagents slowly, and by cooling the solution. After filtration, the solution contained roughly 30 wt % silver, and had a specific gravity of 1.52 g/mL.

Catalyst Preparation (500 ppm Cs)

A 150 g portion of the selected bimodal carrier was placed in a flask and evacuated to ca. 0.1 torr prior to impregnation. To the above silver solution were added aqueous solutions of cesium hydroxide, perrhenic acid, and ammonium sulfate in order to prepare a catalyst composition according to the examples of U.S. Pat. No. 4,766,105 with respect to all catalyst components except cesium. After thorough mixing, the promoted silver solution was aspirated into the evacuated flask to cover the carrier while maintaining the pressure at ca. 0.1 torr. The vacuum was released after about 5 minutes to restore ambient pressure, hastening complete penetration of the solution into the pores. Subsequently, the excess impregnation solution was drained from the impregnated carrier. Calcination of the wet catalyst was done on a moving belt calciner. In this unit, the wet catalyst is transported on a stainless steel belt through a multi-zone furnace. All zones of the furnace are continuously purged with pre-heated, ultra-high purity nitrogen and the temperature is increased gradually as the catalyst passes from one zone to the next. The heat is radiated from the furnace walls and from the preheated nitrogen.

The wet catalyst entered the furnace at ambient temperature. The temperature was then increased gradually to a maximum of about 450° C. as the catalyst passed through the heated zones. In the last (cooling) zone, the temperature of the now activated was immediately lowered to less than 100° C. before it emerged into ambient atmosphere. The total residence time in the furnace was approximately 45 minutes.

All other catalysts were prepared in the same manner except that the amount of aqueous cesium hydroxide solution was adjusted to achieve the desired cesium concentration of the final catalyst.

Testing of the Catalyst

For testing, the catalysts were charged into a fixed-bed stainless steel tube reactor (¼ inch approximate inner diameter), which was embedded in a heated copper block. The catalyst charge consisted of 9 g crushed catalyst (1.0-1.4 mm particle size) and the inlet gas flow was adjusted to give a gas hour space velocity of 5500 h-1. The feed gas composition by volume was 15% ethylene, 7% oxygen, 5% carbon dioxide, 1.7 ppmv ethyl chloride, and nitrogen balance. Reaction pressure was maintained at 19.4 atm. The reactor effluent was analyzed by mass spectrometry at roughly 1-hour intervals. The feed gas was introduced at 200° C. heating temperature and the temperature was increased to reach a desired value of 2.5% EO in the reactor outlet which corresponds to a productivity of 486 g-EO per kg-catalyst per hour. Subsequently, the reaction temperature was adjusted by a maximum slope of 2° C./h up to a maximum temperature of 270° C. in order to maintain the desired value 2.5% EO in the reactor outlet. In case of example 1 to 3, the catalysts reached the desired productivity within the temperature range and the time was measured until the temperature reached its maximum of 270° C. and/or the EO in the outlet dropped under the desired value. In case of example 4, the catalyst activity was too low and the EO concentration in the outlet never reached 2.5% up to a temperature of 270° C. The results are summarized in Table 1 below.

TABLE 1

Catalyst Performance for Different Cesium Levels

| Example | Cesium Content (ppm) | Max. Selectivity (%) | Time at desired Δ EO/Productivity (hr) |
|---|---|---|---|
| 1 | 500 (Inventive) | 86.5 | Greater than 100 |
| 2 | 600 (Inventive) | 86.5 | 62 |
| 3 | 650 (Inventive) | 86.3 | 20 |
| 4 | 750 (Outside Invention) | 82 | Catalyst did not reach desired productivity |

As shown in Table 1, the catalyst containing greater than 700 ppm of cesium (i.e., 750 ppm) did not exhibit an effective level of productivity and also exhibited relatively low selectively. The catalysts containing less than 700 ppm of cesium all exhibited at least an effective level of productivity and selectivity. For example, the catalyst containing 650 ppm of cesium exhibited an effective level of productivity and much improved selectivity. The catalyst containing 600 ppm of cesium exhibited an increased level of productivity and a similar selectivity, as compared to the catalyst containing 650 ppm of cesium. The catalyst containing 500 ppm of cesium exhibited a significantly increased level of productivity and the same level of selectivity, as compared to the catalyst containing 600 ppm of cesium.

Furthermore, it is known that rhenium-containing high selectivity catalysts require a conditioning phase prior to commercial use. The conditioning phase serves to render the catalyst operable under the conditions typically employed (i.e., "normal operating conditions"), as known in the art, during commercial operation. The conditioning procedure typically includes an initial phase at high temperature (e.g., a bed temperature of above 250° C. or 260° C.) in an atmosphere containing oxygen for a period of about 5 to 15 hours. After the conditioning phase, the catalyst will show suitable characteristics, including, for example, viable selectivities. In order to compensate for the high activity of the catalyst during the conditioning phase, the feed gas preferably contains a low concentration of ethylene and oxygen. Since the catalyst is characterized by a high activity and low selectivity during the conditioning phase, the product yield and quality tend to be poor.

A significant advantage in using the inventive catalysts described herein is that they can be operated either without the initial conditioning phase or with an initial conditioning phase that can be conducted under less extreme conditions (i.e., closer to or at normal operating conditions). For example, the inventive catalysts described herein can be started up at conditions very close to normal operating conditions, e.g., at temperatures below about 250° C. This advantageously allows the catalyst to operate at full productivity from the very beginning, in contrast to the catalysts of the prior art which are essentially inoperable during the lengthy conditioning phase.

While the present invention has been demonstrated and described with reference to preferred embodiments, it will be readily appreciated by those of ordinary skill in the art that various changes and modifications may be made without departing from the spirit and scope of the invention. It is therefore intended that the claims be interpreted to cover the disclosed embodiment, those alternatives which have been discussed, and any and all equivalents thereto.

What is claimed is:

1. A catalyst useful in the epoxidation of an olefin to an olefin oxide, the catalyst comprising a support having a bimodal pore size distribution of a first distribution of pore sizes and a second distribution of pore sizes wherein each distribution of pore sizes possesses a different mean pore size and a different pore size of maximum concentration, wherein each of said first and second distribution of pore sizes possesses a mean pore size within a range of 0.01 to 4.0 µm, said support having a catalytically effective amount of silver, a promoting amount of rhenium, and cesium in an amount from not less than 350 ppm to up to but not exceeding 500 ppm disposed thereon.

2. The catalyst of claim 1, wherein the first distribution of pores comprises at most 50% of a total pore volume and the second distribution of pores comprises at least 50% of the total pore volume.

3. The catalyst of claim 1, wherein the first distribution of pores comprises at most 40% of a total pore volume and the second distribution of pores comprises at least 60% of the total pore volume.

4. The catalyst of claim 1, wherein the support comprises alumina, charcoal, pumice, magnesia, zirconia, titania, kieselguhr, fuller's earth, silicon carbide, silica, silicon dioxide, magnesia, clays, artificial zeolites, natural zeolites, ceramics or combinations thereof.

5. The catalyst of claim 1, wherein the support comprises alumina.

6. The catalyst of claim 1, wherein the support comprises alumina with a surface area of at most about 1 $m^2/g$.

7. The catalyst of claim 1, further comprising a promoting amount of one or more Group IIA metal promoters.

8. The catalyst of claim 1, further comprising a promoting amount of one or more transition metals other than rhenium.

9. The catalyst of claim 8, wherein the one or more transition metals are selected from the group consisting of Groups IVB, VB, VIB, VIIB, and VIIIB of the Periodic Table of the Elements.

10. The catalyst of claim 8, wherein the one or more transition metals are selected from the group consisting of molybdenum, tungsten, chromium, titanium, hafnium, zirconium, vanadium, thorium, tantalum, and niobium.

11. The catalyst of claim 8, wherein the transition metal is molybdenum, tungsten, or a combination thereof.

12. The catalyst of claim 1, further comprising a promoting amount of one or more alkali metals other than cesium.

13. The catalyst of claim 12, wherein said one or more alkali metals are selected from the group consisting of lithium, sodium, potassium, and rubidium.

14. The catalyst of claim 12, wherein said alkali metal is lithium.

15. The catalyst of claim 1, further comprising a promoting amount of one or more sulfur-containing compounds.

16. The catalyst of claim 1, further comprising a promoting amount of one or more fluorine-containing compounds.

17. The catalyst of claim 1, further comprising a promoting amount of one or more phosphorus-containing compounds.

18. A catalyst useful in the epoxidation of an olefin to an olefin oxide, the catalyst comprising a support having a bimodal pore size distribution of a first distribution of pore sizes and a second distribution of pore sizes wherein each distribution of pore sizes possesses a different mean pore size and a different pore size of maximum concentration, wherein each of said first and second distribution of pore sizes possesses a mean pore size within a range from above 6 µm up to 30 µm, said support having a catalytically effective amount of silver, a promoting amount of rhenium, and cesium in an amount from not less than 350 ppm to up to but not exceeding 500 ppm disposed thereon.

19. The catalyst of claim 18, wherein the first distribution of pores comprises at most 50% of a total pore volume and the second distribution of pores comprises at least 50% of the total pore volume.

20. The catalyst of claim 18, wherein the first distribution of pores comprises at most 40% of a total pore volume and the second distribution of pores comprises at least 60% of the total pore volume.

21. The catalyst of claim 18, wherein the support comprises alumina, charcoal, pumice, magnesia, zirconia, titania, kieselguhr, fuller's earth, silicon carbide, silica, silicon dioxide, magnesia, clays, artificial zeolites, natural zeolites, ceramics or combinations thereof.

22. The catalyst of claim 18, wherein the support comprises alumina.

23. The catalyst of claim 18, wherein the support comprises alumina with a surface area of at most about 1 $m^2/g$.

24. The catalyst of claim 18, further comprising a promoting amount of one or more Group IIA metal promoters.

25. The catalyst of claim 18, further comprising a promoting amount of one or more transition metals other than rhenium.

26. The catalyst of claim 25, wherein the one or more transition metals are selected from the group consisting of Groups IVB, VB, VIB, VIIB, and VIIIB of the Periodic Table of the Elements.

27. The catalyst of claim 25, wherein the one or more transition metals are selected from the group consisting of molybdenum, tungsten, chromium, titanium, hafnium, zirconium, vanadium, thorium, tantalum, and niobium.

28. The catalyst of claim 25, wherein the transition metal is molybdenum, tungsten, or a combination thereof.

29. The catalyst of claim 18, further comprising a promoting amount of one or more alkali metals other than cesium.

30. The catalyst of claim 29, wherein said one or more alkali metals are selected from the group consisting of lithium, sodium, potassium, and rubidium.

31. The catalyst of claim 29, wherein said alkali metal is lithium.

32. The catalyst of claim 18, further comprising a promoting amount of one or more sulfur-containing compounds.

33. The catalyst of claim 18, further comprising a promoting amount of one or more fluorine-containing compounds.

34. The catalyst of claim 18, further comprising a promoting amount of one or more phosphorus-containing compounds.

* * * * *